United States Patent
Kokate et al.

(10) Patent No.: US 6,890,307 B2
(45) Date of Patent: May 10, 2005

(54) CATHETERS WITH FLUORESCENT TEMPERATURE SENSORS

(75) Inventors: Jaydeep Y. Kokate, Maple Grove, MN (US); Eric M. Dobrava, Crystal, MN (US); Scott R. Smith, Chaska, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 297 days.

(21) Appl. No.: 10/043,051

(22) Filed: Jan. 9, 2002

(65) Prior Publication Data

US 2002/0123696 A1 Sep. 5, 2002

Related U.S. Application Data

(60) Provisional application No. 60/272,674, filed on Mar. 1, 2001.

(51) Int. Cl.$^7$ .................................................. A61B 5/00
(52) U.S. Cl. ....................................... 600/549; 600/474
(58) Field of Search ............................... 600/549, 474; 374/100, 131

(56) References Cited

U.S. PATENT DOCUMENTS

| | | | |
|---|---|---|---|
| 4,215,275 A | | 7/1980 | Wickersheim |
| 4,448,547 A | | 5/1984 | Wickersheim |
| 4,560,286 A | | 12/1985 | Wickersheim |
| 4,652,143 A | * | 3/1987 | Wickersheim et al. ...... 374/161 |
| 4,752,141 A | * | 6/1988 | Sun et al. .................... 374/161 |
| 4,895,156 A | | 1/1990 | Schulze |
| 5,012,809 A | * | 5/1991 | Shulze ........................ 600/329 |
| 5,103,804 A | | 4/1992 | Abele et al. |
| 5,122,137 A | | 6/1992 | Lennox |
| 5,151,100 A | | 9/1992 | Abele et al. |
| 5,157,457 A | | 10/1992 | Taylor |
| 5,166,990 A | | 11/1992 | Riccitelli et al. |
| 5,378,234 A | * | 1/1995 | Hammerslag et al. ...... 600/528 |
| 5,405,322 A | | 4/1995 | Lennox et al. |
| 5,439,446 A | | 8/1995 | Barry |
| 5,456,252 A | * | 10/1995 | Vari et al. .................... 600/301 |
| 5,496,311 A | | 3/1996 | Abele et al. |
| 5,497,782 A | * | 3/1996 | Fugoso ........................ 600/585 |
| 5,540,679 A | | 7/1996 | Fram et al. |
| 5,545,195 A | | 8/1996 | Lennox et al. |
| 5,596,988 A | | 1/1997 | Markle et al. |
| 5,617,870 A | | 4/1997 | Hastings et al. |
| 5,685,847 A | | 11/1997 | Barry |
| 5,775,338 A | | 7/1998 | Hastings |
| 5,830,239 A | | 11/1998 | Toomes |
| 5,833,688 A | | 11/1998 | Sieben et al. |
| 5,857,998 A | | 1/1999 | Barry |

(Continued)

FOREIGN PATENT DOCUMENTS

EP          0432262 A1      6/1991

*Primary Examiner*—Eric F. Winakur
*Assistant Examiner*—Matthew Kremer
(74) *Attorney, Agent, or Firm*—Marshall, Gerstein & Borun LLP (57) ABSTRACT

A catheter with a fluorescent temperature sensor is shown and described. The catheter includes a lumen, a fiber-optic cable that extends through the lumen. A distal end of the fiber-optic cable is coated with a fluorescent material and a proximal end of the fiber-optic cable is connected to a console. The console includes a light source for transmitting light through the fiber-optic cable for exciting the fluorescent material. The console further includes a photo multiplier tube for converting light emitted by the excited fluorescent material to a plurality of analog voltage signals. The console further includes a digital oscilloscope linked to the photo multiplier tube for converting the plurality of analog voltage signals to at least one digital signal. The console further includes a processor linked to the digital oscilloscope for converting the at least one digital signal to a temperature value for the distal end of the fiber-optic cable.

18 Claims, 9 Drawing Sheets

U.S. PATENT DOCUMENTS

| | | |
|---|---|---|
| 5,868,735 A | 2/1999 | Lafontaine |
| 5,871,449 A | 2/1999 | Brown |
| 5,873,835 A | 2/1999 | Hastings et al. |
| 5,909,278 A | 6/1999 | Deka et al. |
| 5,916,153 A | 6/1999 | Rhea, Jr. |
| 5,935,075 A | 8/1999 | Casscells et al. |
| 5,954,693 A | 9/1999 | Barry |
| 5,983,125 A * | 11/1999 | Alfano et al. ............... 600/473 |
| 6,023,638 A | 2/2000 | Swanson |
| 6,107,699 A | 8/2000 | Swanson |
| 6,120,496 A | 9/2000 | Whayne et al. |
| 6,123,702 A | 9/2000 | Swanson et al. |
| 6,156,032 A | 12/2000 | Lennox |
| 6,183,468 B1 | 2/2001 | Swanson et al. |
| 6,190,355 B1 | 2/2001 | Hastings |
| 6,377,842 B1 * | 4/2002 | Pogue et al. ............... 600/478 |
| 2003/0114761 A1 * | 6/2003 | Brown ....................... 600/474 |

\* cited by examiner

CATHETERS WITH FLUORESCENT TEMPERATURE SENSORS

CROSS-REFERENCE TO RELATED APPLICATION

This application claims the benefit under 35 U.S.C. § 119(e) of U.S. provisional patent application Ser. No. 60/272,674 filed Mar. 1, 2001, the disclosure of which is incorporated herein by reference.

FIELD OF THE INVENTION

The present invention relates generally to the field of surgical catheters. More specifically, the present invention relates to surgical catheters with temperature sensors. Still more specifically, the present invention relates to catheters with fluorescent temperature sensors and methods of measuring temperatures along arterial walls using a catheter equipped with a fluorescent temperature sensor for detecting and locating inflamed plaque.

BACK GROUND OF THE INVENTION

Measuring the temperature of tissues, veins or other body parts at remote locations during surgical, electrophysiological and other invasive and minimally invasive procedures can provide critical information to the physician or surgeon. One such procedure is the detection and location of inflamed plaque in an artery.

An atherosclerotic plaque is a thickened area in the wall of an artery. Typically, patients who have died of coronary disease may exhibit as many as several dozen atherosclerotic plaques. However, in most instances of coronary disease, it is found that only one of the atherosclerotic plaques has ruptured, fissured, or ulcerated. The rupture, fissure, or ulcer causes a large blood clot to form on the inside of the artery, which may completely occlude the flow of blood through the artery, thereby injuring the heart or brain. A major prognostic and diagnostic dilemma for the cardiologist is how to predict which plaque is about to rupture.

The rupture process is not completely understood, but it is known that the plaques most likely to rupture are those with inflamed surfaces or a high density of activated macrophages and a thin overlying cap. Van der Wal, et al., Circulation 89:36–44 (1994); Shah, et al., Circulation 244 (1995); Davies, et al., Br Heart J 53:363–373 (1985); Farb, et al., Circulation 92:1701–1709 (1995); Van Damme, et al., Cardiovasc Pathol 3:9–17 (1994). Plaques with inflamed surfaces are thought to be located at junctures where pools of cholesterol meet a more cellular and fibrous part of the plaque. Typically, inflammatory cells, which produce heat, have been found at these junctures. Since these inflammatory cells release enzymes capable of degrading the collagen and other components of the extracellular matrix, it is thought that they are crucial to the process of plaque rupture or fissuring.

Thus, plaques which are believed to be at risk of rupturing, or plaques with inflammatory cells, are known to have a higher temperature than the surrounding tissue by 1–2° C. Accordingly, the detection of such inflamed plaques is helpful in the prediction and subsequent prevention of plaque rupture. U.S. Pat. Nos. 5,935,075 and 5,871,449 disclose devices for locating inflamed plaque based upon a temperature measurement. Both patents disclose infrared devices and are not readily adaptable to existing catheter systems.

Another procedure where knowledge of temperature at the precise location of the therapy is ablation, which is the technique used to correct cardiac arrhythmia. Cardiac arrhythmia is an electrical malfunction of the heart. Electrophysiological therapy treats cardiac arrhythmia by ablating the tissue area that is the source of the electrical malfunction. To ablate the tissue, a physician performing the electrophysiological therapy steers an ablation catheter through a vein or an artery into the interior region of the heart. The catheter has an ablating element (e.g., an electrode or a fiber-optic bundle) along the distal end of the catheter which delivers energy (e.g., radio frequencies or laser light) to the targeted tissue. The delivered energy heats the tissue and forms a lesion.

Temperature is a critical parameter in achieving success with the ablation procedure. The lesion size and shape are a function of the temperature of the ablated tissue, the surrounding tissue, and/or the ablating element. Thus, temperature is monitored during the procedure The catheter includes a temperature sensor to measure the temperature of the tissue near the ablating element during the procedure. It is known to use a thermistor or a thermocouple at the end of the catheter to measure the temperature.

The ablation catheter typically is connected to a controller/generator unit by a medical grade cable with an adapter specific to the controller/generator unit. The generator delivers the energy necessary for ablation and the controller receives temperature-related signals from the thermistor or the thermocouple. The controller may further monitor electrical activity of the heart during the ablation procedure. The controller and the generator can be a single unit, or the two functions can be performed by two separate units.

Radio frequency (RF) energy is one type of ablating energy used in electrophysiological therapy. The RF ablation generator/controller units currently available are either thermistor-based or thermocouple-based. That is, known RF generator/controller units can display temperature based on signals provided by a temperature sensor in the catheter, but they can do so only for a particular type of temperature sensor, either a thermistor or a thermocouple. One example of a combination ablation/temperature sensor catheter is disclosed in U.S. Pat. No. 5,833,688, assigned to the assignee of the present application.

Other types of sensors include the use of fiber-optic catheters having a fluorometric sensor at a distal end of the catheter. One example is disclosed in U.S. Pat. No. 5,012,809. Such sensors operate by using a light source to excite fluorescent material disposed at a distal end of the catheter. The excited fluorescent material in turn emits light which is transmitted back through the fiber-optic cable. The lifetime of the fluorescence is used to calculate the temperature at the distal end of the catheter. However, the catheter disclosed in the '809 patent utilizes an incandescent light source, and photodetectors which require the use of amplifiers. The algorithms used to calculate temperature are dependent upon the polymer/fluophor matrix used in construction of the catheter.

U.S. Pat. Nos. 4,448,547 and 4,560,286 also disclose the use of flourescent materials or phosphors to measure temperature. However, the apparatus as disclosed in these patents require the use of a radioactive material or a source of ultraviolet light to excite the phosphor or fluorescent material.

Accordingly, there is a need for an improved fluorescent temperature sensor which can be incorporated into currently available catheter designs in an inexpensive and efficient manner and further which can be operated with minimal trauma to the artery.

SUMMARY OF THE INVENTION

The present invention satisfies the aforenoted needs by provided an improved catheter temperature sensor and method of measuring temperature at a remote location inside a body using a catheter equipped with a temperature sensor.

One disclosed catheter temperature sensor comprises a lumen, a fiber-optic cable that extends through the lumen and a console that is linked to the fiber-optic cable. The fiber-optic cable comprises a distal end that his coated with a fluorescent material in a proximal end that is linked to the console. The console comprises a light source and transmits light through the fiber-optic cables to the fluorescent material to excite the fluorescent material. The excited fluorescent material fluoresces light which is transmitted back through the fiber-optic cable to the console. The console measures a lifetime of the fluoresced light and, based upon the measured lifetime, determines a temperature at the distal end of the fiber-optic cable, or at a point along an arterial wall.

In a refinement of the disclosed sensor, the lumen comprises a distal end section that surrounds the distal end of the fiber-optic cable. The distal end section of lumen is received coaxially in a coil spring. In a related refinement, the lumen further comprises an open distal tip and the coil spring comprises a distal end. The open distal tip of the lumen is connected to and sealed by a weld ball. The weld ball is connected to the distal end of the coil spring. In another related refinement, the coil spring further comprises a proximal end that is welded to an outer surface of the lumen.

In another refinement of the disclosed sensor, the lumen is connected to another lumen which receives a guide wire. In a related refinement, the lumen is connected to the guide wire lumen with shrink wrap. In still another related refinement, the lumen passes through the guide wire lumen.

In another refinement of the disclosed sensor, the sensor comprises a lumen and a fiber-optic cable that extends through the lumen. The fiber-optic cable comprises a distal end connected to a reflecting surface and a proximal end connected to a console. The lumen is connected to a balloon. The balloon surrounds the distal end of the fiber-optic cable and the reflecting surface. The balloon further comprises an interior surface that is at least partially coated with fluorescent material. The console comprises a light source for transmitting light through the fiber-optic cable to the distal end thereof. The reflecting surface reflects light transmitted through the fiber-optic cable to the interior surface of the balloon thereby exciting the fluorescent material and causing fluoresced light to be transmitted back from the interior surface of the balloon to the reflecting surface, through the fiber-optic cable to the console. The console measures a lifetime of the fluoresced light and converts the lifetime to a temperature of the balloon.

In a further refinement, the disclosed sensor comprises a lumen and a guide wire that passes through the lumen. At least one fiber-optic cable is annularly spaced between the guide wire and the lumen. The fiber-optic cable comprises a distal end coated with a fluorescent material and a proximal end connected to a console. The lumen is retractable with respect to the guide wire and the fiber-optic cable. The fiber-optic cable is biased radially outwardly from the guide wire so that when the lumen is retracted, the distal end of the fiber-optic cable will move away from the guide wire. In practice, the distal end of the fiber-optic cable will move away from the guide wire and towards the arterial wall. The console calculates the temperature of the distal end of the fiber-optic cable in a manner as discussed above.

In a further refinement, the disclosed sensor comprises a plurality of fiber-optic cables spaced around the guide wire and annularly between the guide wire and the lumen. The fiber-optic cables are biased radially outwardly so that when the lumen is retracted, the distal ends of the fiber-optic cables move radially away from the guide wire and towards the arterial wall. In a preferred embodiment of this refinement, the console will calculate a temperature for each distal end for each fiber-optic cable thereby providing a circumferential temperature profile of the arterial wall.

In another refinement of the disclosed sensor, the sensor comprises a lumen comprising a distal end connected to a balloon. Preferably, a guide wire passes through the lumen. At least one fiber-optic cable extends along the outer surface of the lumen and has a distal end that is disposed on the outer surface of the balloon. The distal end of the fiber-optic cable is coated with a fluorescent material and the proximal end of the fiber-optic cable is connected to a console as discussed above. As the balloon is inflated, the distal end of the fiber-optic cable engages the arterial wall.

In a further refinement of the above concept, a plurality of fiber-optic cables are spaced circumferentially around the outer surfaces of the lumen and balloon thereby providing a circumferential profile of the temperature of the arterial wall.

In another refinement, the lumen comprises a compressible section allowing the lumen to assume a retracted position and an extended position. The distal end section of the lumen also comprises a side opening. The distal end of the fiber-optic cable is aligned with the side opening and extends through the side opening when the lumen is in the retracted position. When the lumen is in the extended position, the distal end of the fiber-optic cable is disposed within the lumen. In a further refinement of this concept, the distal end section of the lumen comprises a plurality of side openings and the sensor comprises a plurality of fiber-optic cables. Each fiber-optic cable extending through one of the side openings of the lumen when the lumen is in the retracted position and each fiber-optic cable be disposed within the lumen when the lumen is in the extended position. In still a further refinement of this concept, the lumen may accommodate a conical insert disposed within the lumen that serves to guide the fiber-optic cables in and out of the side openings as the lumen is extended and retracted.

In another refinement, the distal end section of the lumen comprises a side opening and the lumen is accommodated in a retractable sheath. The distal end of the fiber-optic cable extends through the side opening of the lumen and is surrounding by the sheath when the sheath is not retracted. The sheath can be retracted to expose the distal end of the fiber-optic cable and, in a preferred refinement, the distal end of the fiber-optic cable is spring biased in a radially outward manner so that it engages a sidewall of a vessel or organ when the sheath is retracted. In a further refinement of this concept, a plurality of side holes and spring biased fiber-optic cables are provided.

In a related refinement, the distal end section of the lumen includes a side opening through which the distal end of the fiber-optic cable extends. An exterior surface of the lumen comprises a slot or groove for accommodating the distal end of the fiber-optic cable to provide a streamlined profile. In a further refinement of this design, a plurality of side openings and slots or grooves are provided along with a plurality of fiber-optic cables.

In another refinement of the disclosed sensor, the console comprises a light source for transmitting light through the fiber-optic cable and for exciting the fluorescent material.

The console further comprises a photo multiplier tube for converting light emitted by the excited fluorescent material to a plurality of analogue voltage signals. The console further comprises a digital oscilloscope linked to the photo multiplier tube for converting the plurality of analogue voltage signals to at least one digital signal. The console also comprises a processor linked to the digital oscilloscope for converting the at least one digital signal to a temperature of the distal end of the fiber-optic cable.

In another refinement of the disclosed sensor, the light source further excites the fluorescent material for a first time period and then stops the excitation. After the excitation stops, the intensity of the light emitted by the excited fluorescent material decays as a function of temperature resulting in changes in the analogue voltage signals generated by the photo multiplier tube.

In another refinement of the disclosed sensor, the processor comprises a memory comprising at least one table for correlating the at least one digital signal to the temperature of the distal end of the fiber-optic cable.

In another refinement the disclosed sensor, the light source is a laser. In a further refinement, the light source is a nitrogen laser.

In another refinement of the disclosed sensor, the sensor further comprises a beam splitter disposed at the proximal end of the fiber-optic cable. The beam splitter is linked to the light source and the photo multiplier tube. The beam splitter transmits light from the light source to the fiber-optic cable and also transmits light emitted by the excited fluorescent material from the fiber-optic cable to the photo multiplier tube.

In another refinement of the disclosed sensor, the sensor further comprises a trigger delay generator linked to the light source.

In another refinement, the sensor further comprises a filter disposed between proximal end of the fiber-optic cable and the photo multiplier tube.

In another refinement, the sensor further comprises a band space filter disposed between the proximal end of the fiber-optic cable and the photo multiplier tube.

In another refinement, the sensor further comprises a band space filter disposed between a beam splitter and the photo multiplier tube.

In another refinement, the fluorescent material comprises magnesium fluorogermanate.

In another refinement, the fluorescent material comprises magnesium fluorogermanate doped with manganese.

In another refinement, the flourescent material comprises lanthanum oxysulfide.

In another refinement, the flourescent material comprises lanthanum oxysulfide doped with europium.

In another refinement, the flourescent material comprises a doped phosphor.

A method for determining a temperature along an arterial wall is also disclosed. The disclosed method includes providing a catheter that comprises a lumen and a fiber-optic cable that extends through the lumen. The fiber-optic cable comprises a distal end coated with a fluorescent material. The fiber-optic cable also comprises a proximal end. The method further includes the step of inserting the catheter into the artery and, for a first predetermined time period, transmitting light through the fiber-optic cable to the fluorescent material thereby exciting the fluorescent material and causing it to fluoresce. The method further includes the step of stopping the transmission of light through the fiber-optic cable. The method also includes the step of receiving light emitted by the excited fluorescent material through the fiber-optic cable at the proximal end of the fiber-optic cable for a second predetermined time period. The method also includes the step of measuring a lifetime of the fluoresced light received at the proximal end of the fiber-optic cable and converting the measured lifetime of the fluoresced light to a temperature value.

It should be understood that the drawings are not necessarily to scale and that the embodiments are sometimes illustrated using graphic symbols, phantom lines, diagrammatic representations and fragmentary views. In certain instances, details which are not necessary for an understanding of the disclosed embodiments or which render other details difficult to perceive may have been omitted. It should be understood, of course, that the invention is not necessarily limited to the particular embodiments illustrated herein.

DETAILED DESCRIPTION OF THE PRESENTLY PREFERRED EMBODIMENTS

Phosphors consist of inorganic oxides, oxysulfides, orthophosphates and rare earth metals. Phosphors typically contain a small concentration of a dopant. When excited by certain wavelengths of light, phosphors will fluoresce and the decay time of the fluorescents is proportional to the temperature of the phosphor. As the temperature increases, typically, the decay time decreases for a particular emission wavelength.

Preferred phosphors used in the disclosed embodiments include manganese doped magnesium fluorogermanate and europium doped lanthanum oxysulfide. These phosphors have peak emission intensities at 514 nm, 538 nm and 619 nm.

Figure 1:
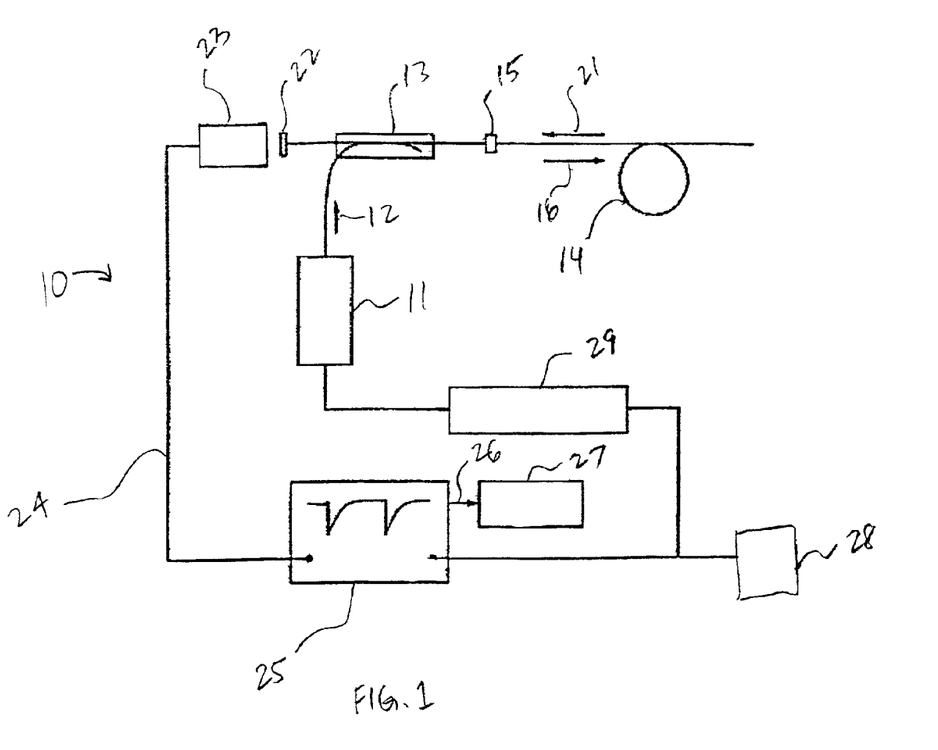
FIG. 1 illustrates, schematically, a catheter and fluorescent temperature sensor system made in accordance with the present invention.

In the embodiment illustrated in FIG. 1, the system 10 utilizes a light source 11, which is preferably a laser, more preferably a nitrogen laser. The light source 11 preferably emits ultraviolet light which is transmitted in the direction of the arrow 12 through a beam splitter 13. The beam splitter 13 is connected to a fiberoptic cable 14 at a connector 15. The ultraviolet light is transmitted in the direction of the arrow 16.

As shown in FIGS. 2–5, the distal end sections 17a–17c of the fiber-optic cables 14a–14c are coated with a fluorescent material 18. The ultraviolet light generated by the light source 11 and transmitted down the fiber-optic cables 14a–14c excite the phosphor material 18 thereby causing it to fluoresce. The fluoresced light or emission is transmitted back towards a proximal end of the fiber-optic cable in the direction of the arrow 21 (see FIG. 1) and passes through the beam splitter 13 and filter 22 before being received at a photo multiplier tube 23.

The photo multiplier tube 23 converts the light emitted by the phosphor material 18 to a plurality of voltage signals which are transmitted through the line 24 to a digital oscilloscope 25. The digital oscilloscope 25 converts the voltage signals to a digital signal and transmits the digital signal through the line 26 to a processor 27. In one embodiment, the processor 27 may be a laptop computer. A control room 28 may be utilized to send a signal to a trigger delay generator 29 which, in turn, sends a signal to the light source 11 to emit light.

Contemporaneously, the signal is sent to the oscilloscope 25 to cease sending digital signals to the processor 27. After a predetermined time period of excitation of the fluorescent material 18, the light source 11 is shut off and fluoresced light emitted by the fluorescent material 18 is then received at the photo multiplier tube 23 which for a predetermined time period, sends voltage signals to the oscilloscope 25 which, in turn, sends at least one digital signal to the processor 27. In one embodiment, the digital signal received by the processor represents a change in the voltage signals received at the oscilloscope which are compared to tabulated values of the exponential delay curve stored in the memory of the processor 27 for converting the digital signal to a temperature value. The precursor may also utilize an algorithm for calculating the temperature. Such algorithms are known to those skilled in the art (see, e.g., U.S. Pat. No. 5,012,809).

Figure 2:
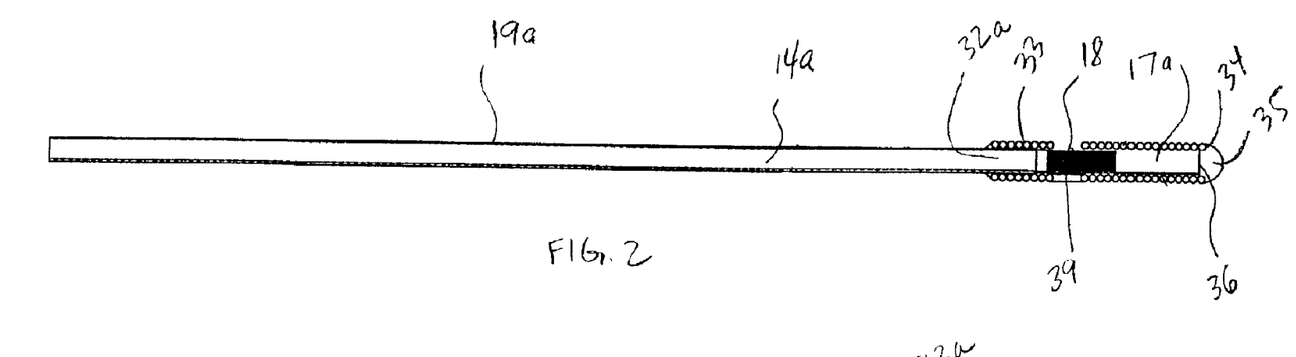
FIG. 2 is a side sectional view of a catheter tip made in accordance with the present invention.
Figure 3:
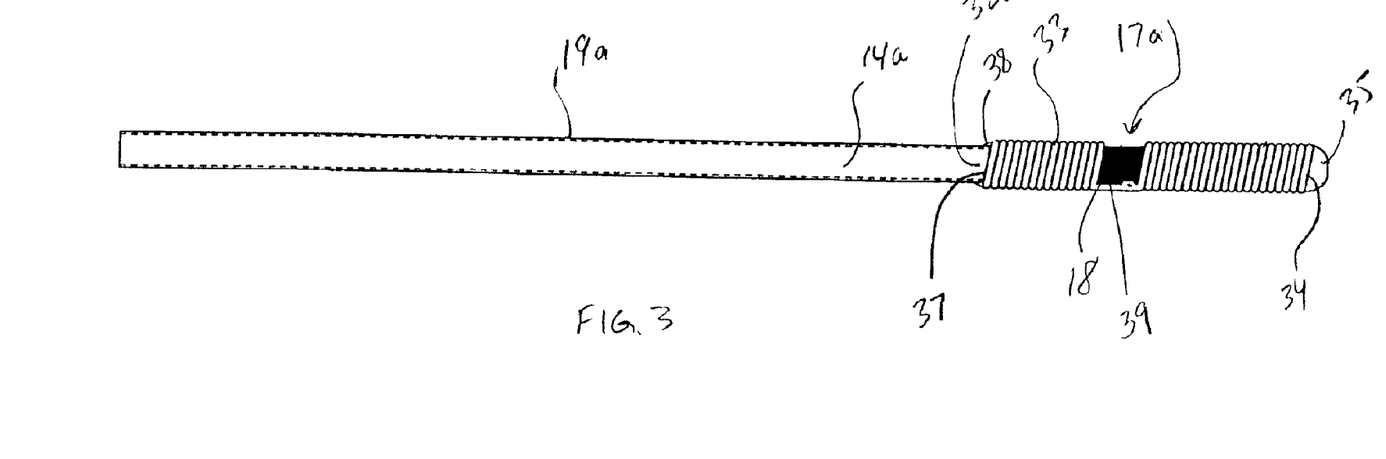
FIG. 3 is a side plan view of the catheter tip shown in FIG. 2.
Figure 4:
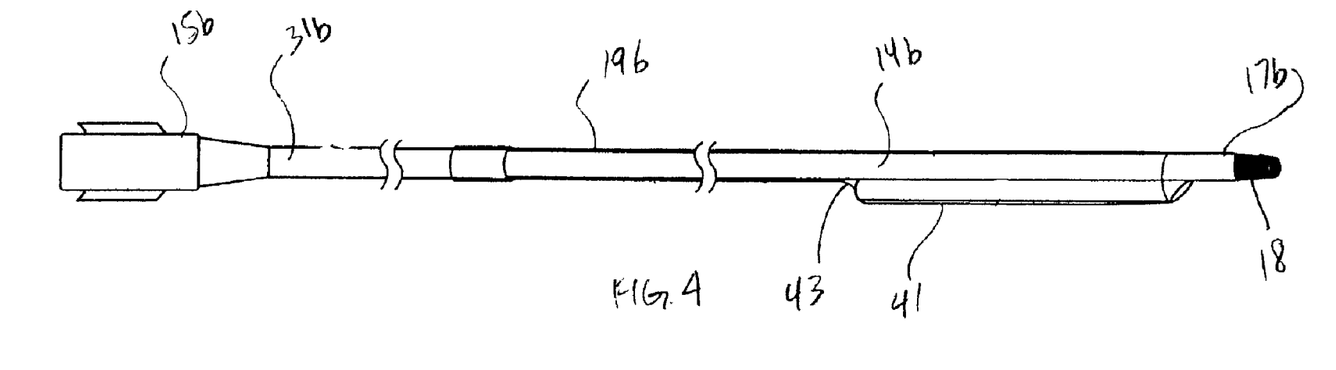
FIG. 4 is a perspective view of another catheter tip made in accordance with the present invention.
Figure 5:
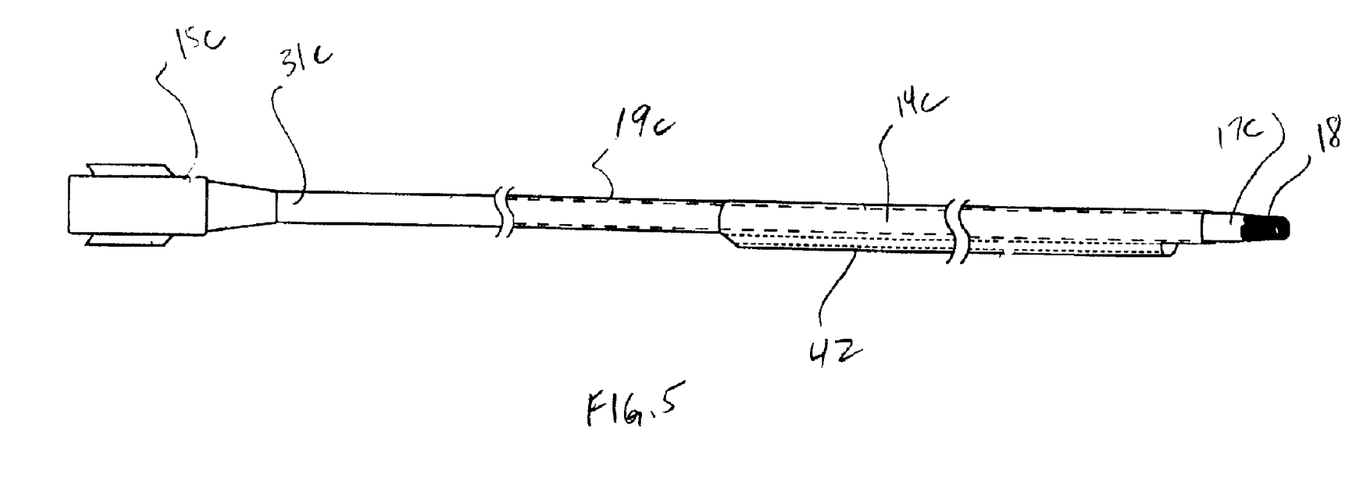
FIG. 5 is a perspective view of yet another catheter tip made in accordance with the present invention.

Turning to FIGS. 2–5, the fiber-optic cables 14a–14c are disposed within lumens 19a–19c. As shown in FIGS. 4 and 5, the proximal ends 31b, 31c of the lumens 19b, 19c are connected to connectors 15b, 15c.

As shown in FIGS. 2 and 3, the distal end section 32a of the lumen 19a passes through a coil 33. A distal end 34 of the coil is connected to a weld ball 35 which seals a distal tip 36 of the lumen 19a. A proximal end 37 of the coil 33 is welded to an outer surface of the lumen 19a at the weld 38. As shown in FIGS. 2 and 3, a gap is provided in the coil 33 at the fluorescent material 18 so that the coil 18 does not insulate the fluorescent material 18 to provide uninhibited heat conductance to the phosphor material 18 and therefore an accurate temperature measurement. The wire ribbon 39 is disposed beneath the coil 33 to keep the coil 33 from spreading. The use of the coil 33 and ribbon 39 provides superior heat conductance to the phosphor material 18 as well as structural integrity while maintaining a small profile to provide a thermal probe that operates in a minimally traumatic fashion.

As shown in FIGS. 4 and 5, the fluorescent material 18 may be completely exposed. In the embodiments illustrated in FIGS. 4 and 5, the lumens 19b and 19c respectively are connected to guide wire lumens 41 and 42 respectively. The guide wire lumen 41 is secured to the lumen 19b with shrink wrap 43. In contrast, referring to FIG. 5, the lumen 19c passes through the guide wire lumen 42. Similar to the embodiment shown in FIGS. 2–3, the embodiments shown in FIGS. 4–5 provide a slim, streamlined thermal sensor that causes minimal trauma during use.

Figure 6:
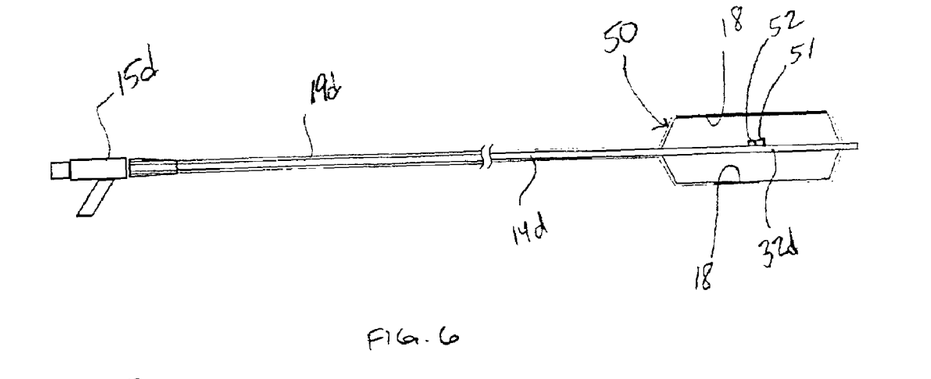
FIG. 6 is a side sectional view of yet another catheter tip made in accordance with the present invention.

Turning to FIG. 6, the lumen 19d is connected to a balloon 50. A fiber-optic cable 14d passes through the lumen 19d and through the balloon 50. A reflective surface 51 is provided at a distal end section 32d of the fiber-optic cable 14d which reflects light transmitted down through the fiber-optic cable 14d from the console towards the fluorescent material 18 shown on an interior surface of the balloon 50. As the fluorescent material 18 gets excited, it fluoresces light back towards the reflective surface 51 which, in turn, transmits the fluoresced light through the fiber-optic cable 14d towards the console as discussed above. A separate detector 52 may or may not be disposed at the distal end section 32d of the fiber-optic cable 14d. In the embodiments shown in FIG. 6, the fiber-optic cable 14d acts as a guide wire and, hence, a separate guide wire is not necessary.

Figure 7:
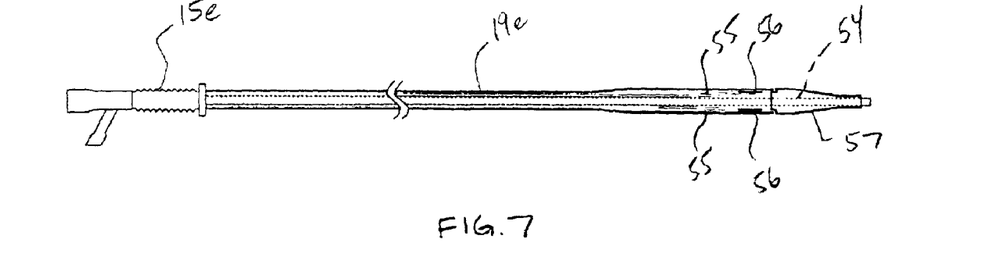
FIG. 7 is a side sectional view of yet another catheter tip made in accordance with the present invention.
Figure 8:
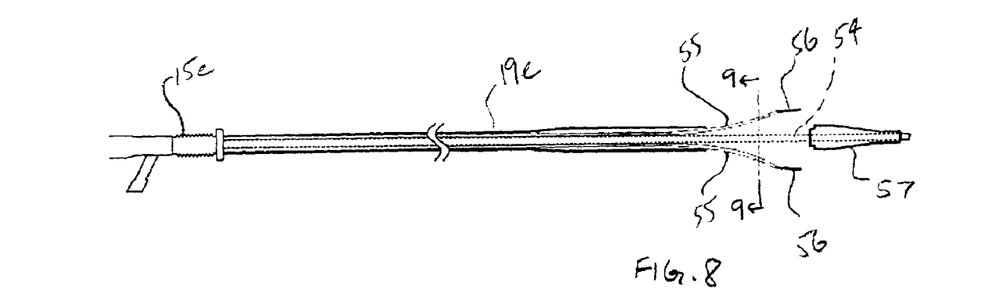
FIG. 8 is another side sectional view of the catheter tip shown in FIG. 7 with the sleeve in a retracted position and with the temperature probes in a radially expanded position.
Figure 9:
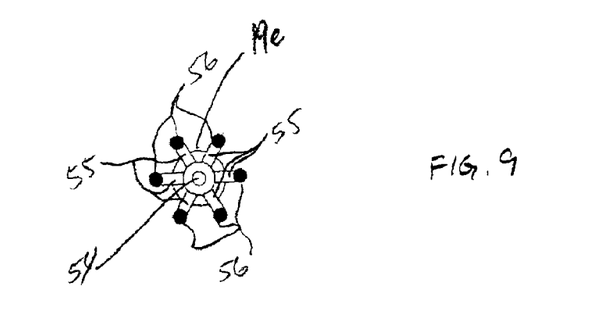
FIG. 9 is a sectional view taken substantially along the line 9—9 of FIG. 8.

In the embodiment shown in FIGS. 7–9, a lumen 19e encases a guide wire shown in phantom at 54 and a plurality of fiber-optic cables shown at 55. As shown in FIG. 8, the fiber-optic cables 55 are biased radially outwardly from the guide wire 54. Accordingly, as the lumen 19e or sheath is retracted, the fiber-optic cables 55 extend outward towards the arterial wall and the fluorescent material-coated distal ends 56 of the fiber-optic cables 55 engage the arterial wall and measure the temperature at different circumferential points of the arterial wall as shown in FIG. 9. Accordingly, the embodiment shown in FIGS. 7–9 can provide a circumferential temperature profile of the arterial wall. The tapered nose piece 57 is detachably connected to the lumen 19e and facilitates in the reduction of trauma to the artery as the catheter illustrated in FIGS. 7–9 is inserted through an artery.

Figure 10:
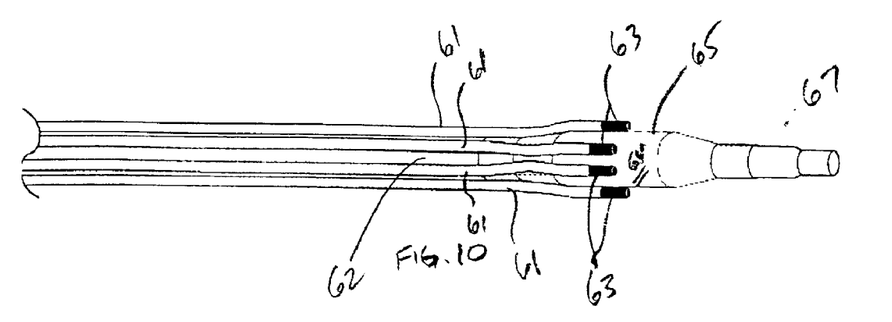
FIG. 10 is a perspective view of a balloon catheter equipped with a plurality of temperature probes made in accordance with the present invention.
Figure 11:
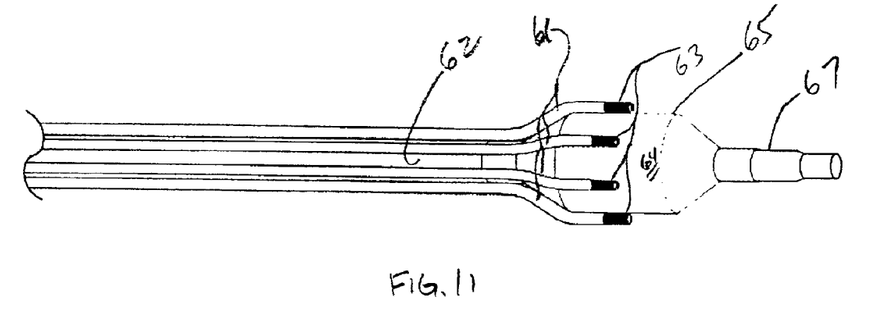
FIG. 11 is another perspective view of the catheter tip shown in FIG. 10 but with the balloon in an expanded state.

In another embodiment directed toward multiple sensors, referring to FIGS. 10–11, a plurality of fiber-optic cables 61 are disposed around a lumen 62. Each fiber-optic cable 61 has a fluorescent material-coated distal end 63 disposed on an exterior surface 64 of a balloon 65. The balloon is connected to the lumen 62. As the balloon 65 is inflated, as shown in FIG. 11, the fluorescent material-coated distal ends 63 of the fiber-optic cables 61 will engage the arterial wall and provide the circumferential temperature profile as discussed above. The tapered nose piece 67 provides a slim profile thereby enabling the catheter illustrated in FIGS. 10–11 to be inserted through an artery with minimal trauma.

Figure 12:
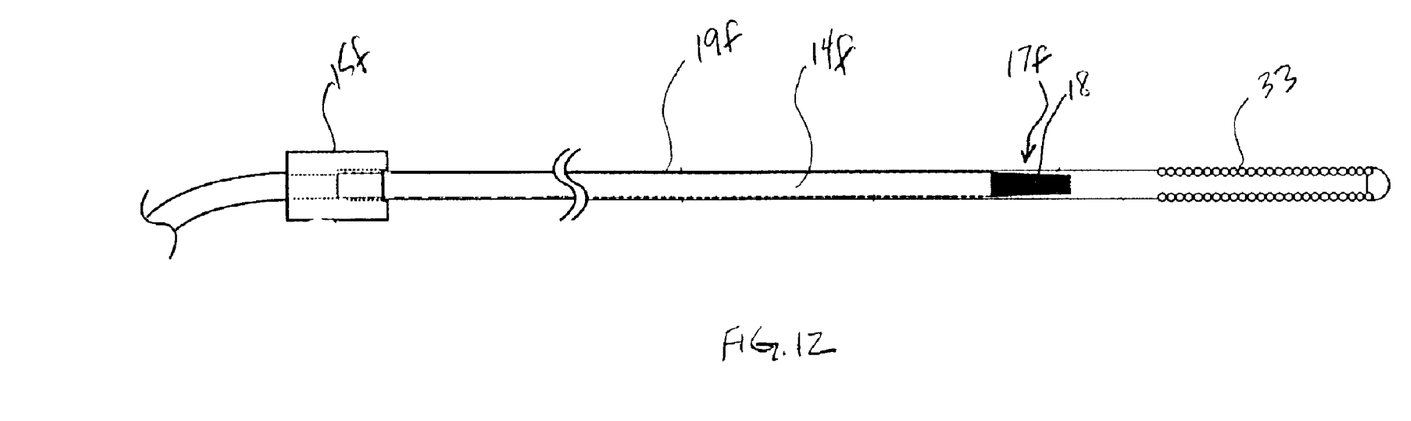
FIG. 12 is a side sectional view of another catheter tip made in accordance with the present invention.
Figure 13:
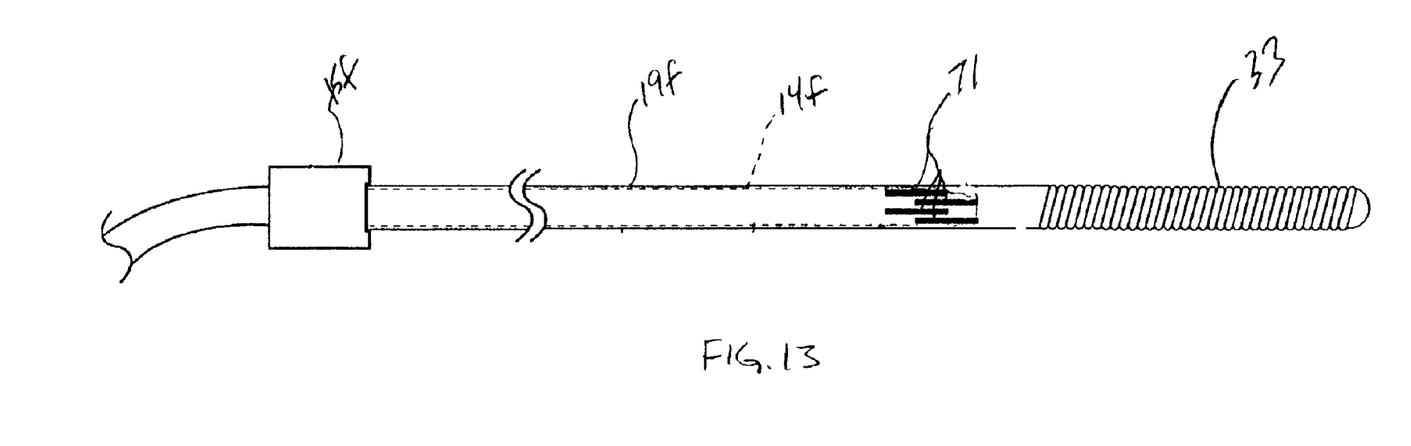
FIG. 13 is a side view of the catheter tip shown in FIG. 12.

Turning to FIGS. 12 and 13, the lumen 19f is similarly connected to a spring 33. The fiber-optic cable 14f is disposed within the lumen 19f and its distal end 17f is disposed proximal to the spring 33. As shown in FIG. 13, the lumen 19f includes a plurality of slots or slits 71 that provide enhanced heat transfer to the distal end 17f of the fiber-optic cable 14f and therefore to the fluorescent material 18. The fiber-optic cable 14f is connected to the lumen 19f by way of the connector 15f.

Figure 14:
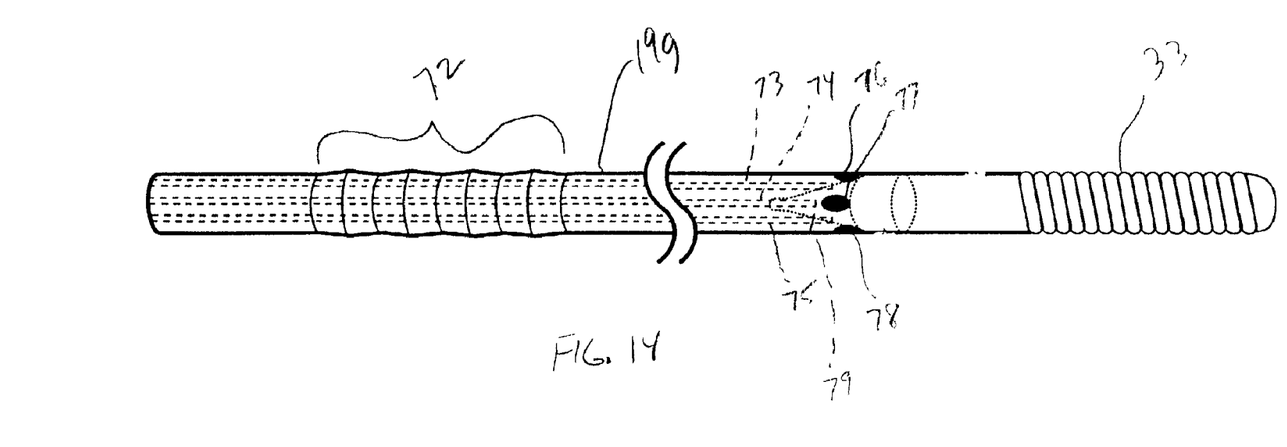
FIG. 14 is a side view of another catheter tip made in accordance with the present invention, in an extended position.
Figure 15:
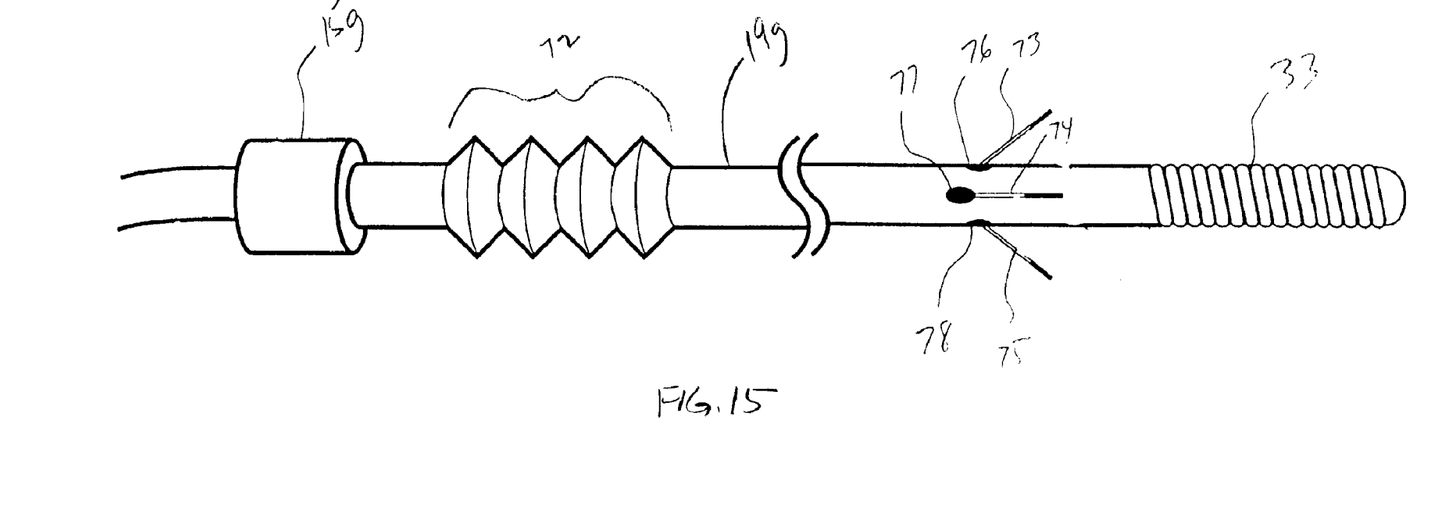
FIG. 15 is a side view of the catheter tip shown in FIG. 4, in a retracted position.

Turning to FIGS. 14–15, an expandable lumen 19g is disclosed. Specifically, the lumen 19g includes an expandable section 72 which has an accordion-like structure. A plurality of fiber-optic cables 73, 74 and 75 are also shown. The fiber-optic cables 73–75 are in alignment with side openings 76, 77 and 78, respectively. In the extended position shown in FIG. 14, the lumen 19 is extended and the fiber-optic cables 73–75 are disposed within the lumen 19g. However, when the lumen 19g is contracted or retracted to the position shown in FIG. 15, the fiber-optic cables 73–75, which are connected to the lumen 19g by way of the connector 15g, extend out through the openings 76–78 and assume the position shown in FIG. 15. The distal ends of the fiber-optic cables 73–75 are spring biased in a radially outwardly manner by the conical insert 79 shown in FIG. 14. Specifically, the conical insert 79 serves to guide the cable 73–75 towards the openings 76–78 and out through the openings in a radially outwardly manner as shown in FIG. 15. In the embodiments shown in FIGS. 14–15, the lumen 19g is also connected to a spring 33. Also, while only three cables 73–75 and three openings 76–78 are shown, a fourth cable and opening are not shown in FIGS. 14–15. The number of cables and openings may range from one to six, while three or four is preferred.

Figure 16:
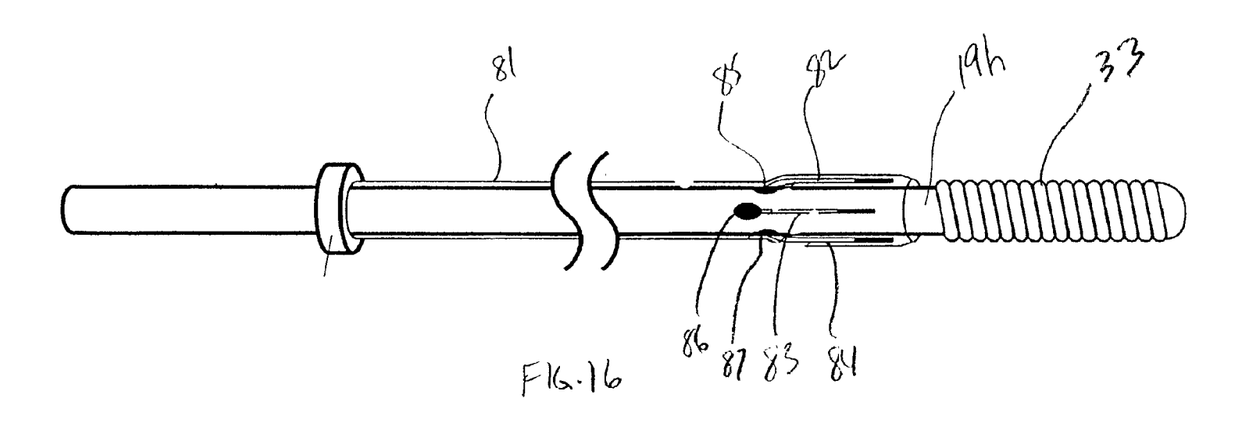
FIG. 16 is a side view of yet another catheter tip made in accordance with the present invention, with a sheath surrounding the distal ends of the fiber-optic cables.
Figure 17:
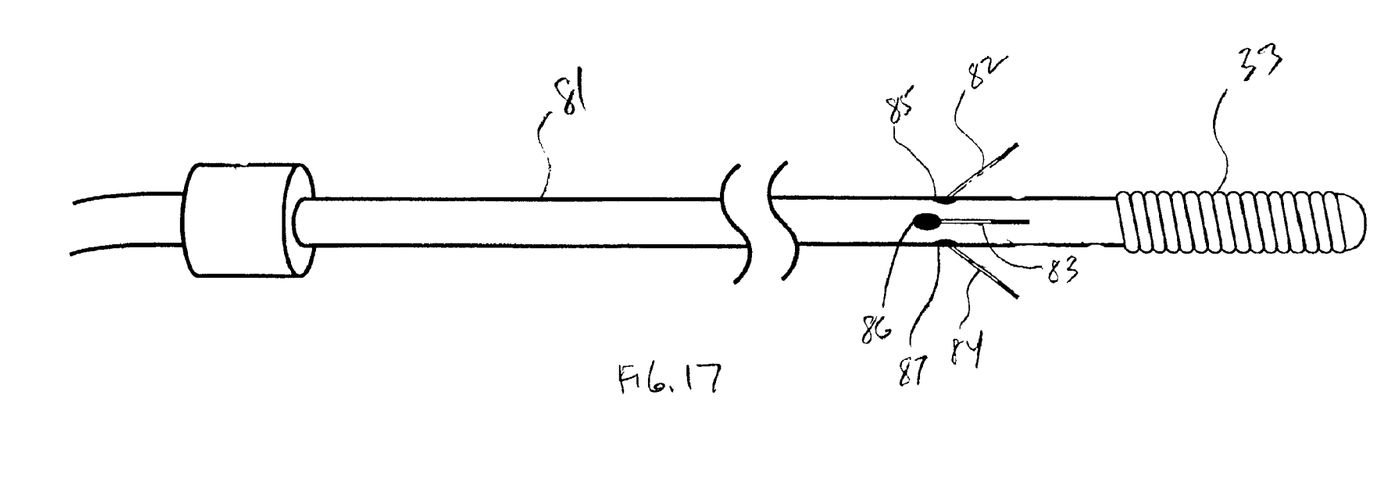
FIG. 17 is a side view of the catheter tip shown in FIG. 16, with the sheath retracted and the distal ends of the fiber-optic cables extended radially outwardly.

Turning to FIGS. 16–17, a lumen 19h is disclosed which is accommodated within an outer sheath 81. Similar to the embodiment in FIGS. 14–15, a plurality of fiber-optic cables 82–84 are disclosed which extend through side openings 85–87 in the lumen 19h. The lumen 19h is also connected to a spring 33. The sheath 81 is retractable and, when retracted or removed as shown in FIG. 17, the fiber-optic cables 82–84 are biased outwardly either by including spring-biasing properties of their own or by way of an insert, such as the conical insert 79 as shown in FIG. 14. Again, anywhere from one to six cables and openings may be employed.

Figures 18, 18A:
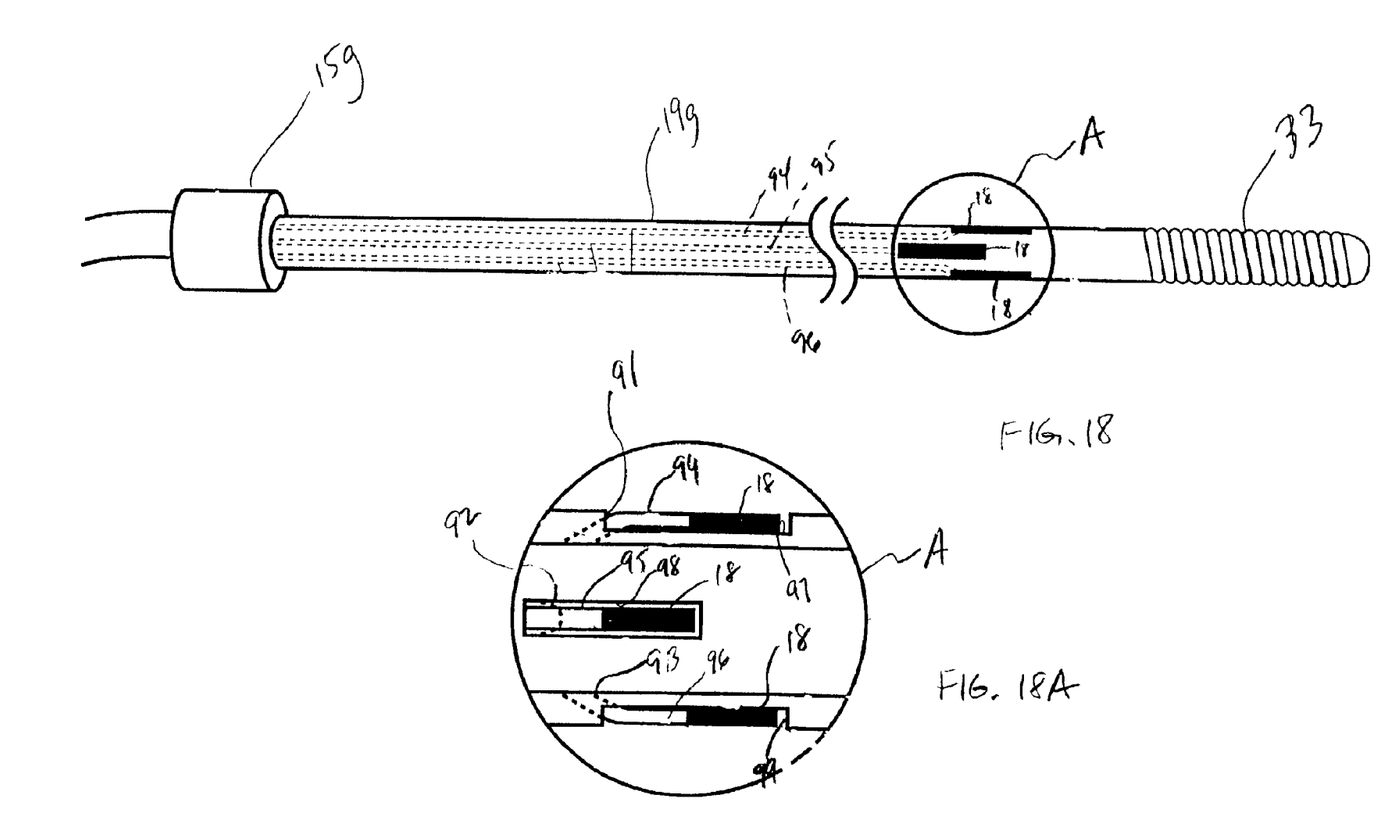
FIG. 18 is a side view of yet another catheter tip made in accordance with the present invention.
FIG. 18A is an enlarged view of the detail A of FIG. 18.

In the embodiment shown in FIGS. 18 and 18A, a lumen 19g is disclosed which includes openings 91–93 through which the fiber-optic cables 94–96 extend. In addition to the openings 91–93, the exterior surface of the lumen 19g includes slots or grooves 97–99 which accommodate the distal ends of the fiber-optic cables 94–96. The fiber-optic cables 94–96 remain in their positions in the slots 97–99. The embodiment illustrated in FIGS. 18 and 18A provides a narrow cross-sectional profile for minimizing trauma to the patient during use. Again, the embodiment shown in FIGS. 18 and 18A include a spring tip 33 and anywhere from one to six cables, openings and slots may be employed.

Variations, modifications and other implementations of what is described herein will be apparent to those of ordinary skill in the art without departing from the spirit and scope of the invention as claimed. Accordingly, the invention is to be defined not by the preceding illustrative description, but instead by the spirit and scope of the following claims.

What is claimed:

1. A catheter temperature sensor comprising:
    a lumen,
    a fiber-optic cable that extends through the lumen, the fiber-optic cable comprising a distal end coated with a fluorescent material and a proximal end connected to a console,
    the lumen comprising a distal end section that at least partially surrounds the distal end of the fiber-optic cable, at least a portion of the distal end section of the lumen being received in a coil spring, the coil spring comprising a series of closely spaced or abutting coils with a gap in the series of coils that is aligned with the fluorescent material, the lumen comprising an opening aligned with the fluorescent material, the gap in the coils and the opening in the lumen permitting unimpeded heat flow to and from the fluorescent material, and
    the console comprising a light source for transmitting light through the fiber-optic cable and exciting the fluorescent material, the console further comprising means for generating a temperature signal from the light emitted by the excited fluorescent material.

2. The sensor of claim 1 wherein the means for generating comprises:
    a photo multiplier tube for converting light emitted by the excited fluorescent material to a plurality analogue voltage signals,
    a digital oscilloscope linked to the photo multiplier tube for converting the plurality of analogue voltage signals to at least on digital signal, and
    a processor linked to the digital oscilloscope for converting the at least one digital signal to a temperature at the distal end of the fiber-optic cable.

3. The sensor of claim 2 wherein the light source further excites the fluorescent material for a first time period and then stops the excitation, after the excitation stops, the intensity of the light emitted by the excited fluorescent material decays as a function of temperature resulting in changes in the analogue voltage signals generated by the photo multiplier tube.

4. The sensor of claim 3 wherein the processor comprises a memory comprising at least one table for correlating the at least one digital signal to the temperature of the distal end of the fiber-optic cable.

5. The sensor of claim 2 further comprising a beam splitter disposed at the proximal end of the fiber-optic cable, the beam splitter being linked to the light source and the photo multiplier tube for transmitting light from the light source to the fiber-optic cable and for transmitting light emitted by the excited fluorescent material from the fiber-optic cable to the photo multiplier tube.

6. The sensor of claim 2 further comprising a filter disposed between the proximal end of the fiber-optic cable and the photo multiplier tube.

7. The sensor of claim 2 further comprising a band space filter disposed between the proximal end of the fiber-optic cable and the photo multiplier tube.

8. The sensor of claim 1 wherein the light source is a nitrogen laser.

9. The sensor of claim 1 wherein the light source is a nitrogen laser.

10. The sensor of claim 1 further comprising a trigger delay generator linked to the light source.

11. The sensor of claim 1 wherein the fluorescent material comprises magnesium fluorogermanate.

12. The sensor of claim 1 wherein the fluorescent material comprises magnesium fluorogermanate doped with manganese.

13. The sensor of claim 1 wherein the fluorescent material comprises lanthanum oxysulfide.

14. The sensor of claim 1 wherein the fluorescent material comprises lanthanum oxysulfide doped with europium.

15. The sensor of claim 1 wherein the fluorescent material comprises a doped phosphor.

16. The sensor of claim 1 wherein the lumen further comprises an open distal tip and the coil spring comprises a distal end, the open distal tip of the lumen being connected to and sealed by a weld ball, the weld ball being connected to the distal end of the coil spring.

17. The sensor of claim 16 wherein the coil spring further comprises a proximal end that is welded to an outer surface of the lumen.

18. A catheter temperature sensor comprising:

a lumen, a fiber-optic cable that extends through the lumen, the fiber-optic cable comprising a distal end coated with a fluorescent material and a proximal end connected to a console, The lumen comprising a distal end section that at least partially surrounds the distal end of the fiber-optic cable, at least a portion of the distal end section of the lumen being received coaxially in a coil sprint, the coil spring comprising a series of closely spaced or abutting coils with a gap in the series of coils that is aligned with the fluorescent material, the lumen comprising an opening aligned with the fluorescent material, the gap in the coils and the opening in the lumen permitting unimpeded heat flow to and from the fluorescent material.

* * * * *